(12) United States Patent
Petit et al.

(10) Patent No.: US 8,894,693 B2
(45) Date of Patent: Nov. 25, 2014

(54) ORTHOPAEDIC FIXATION COMPONENT AND METHOD

(75) Inventors: Yvan Petit, St-Mathieu de Beloeil (CA); Georges Yves Laflamme, Montreal (CA); Yan Bourgeois, St-Mathieu de la Prairie (CA)

(73) Assignees: Valorisation Recherche HSCM, Limited Partnership, Montreal (CA); Ecole de Technologie Superieure, Montreal (CA)

( * ) Notice: Subject to any disclaimer, the term of this patent is extended or adjusted under 35 U.S.C. 154(b) by 1451 days.

(21) Appl. No.: 12/289,755

(22) Filed: Nov. 3, 2008

(65) Prior Publication Data

US 2009/0312758 A1 Dec. 17, 2009

Related U.S. Application Data

(60) Provisional application No. 61/129,221, filed on Jun. 12, 2008.

(51) Int. Cl.
*A61B 17/80* (2006.01)
*A61B 17/82* (2006.01)
*A61B 17/74* (2006.01)
*A61B 17/00* (2006.01)

(52) U.S. Cl.
CPC ....... *A61B 17/82* (2013.01); *A61B 2017/00867* (2013.01); *A61B 17/74* (2013.01); *A61B 17/809* (2013.01)
USPC ............. 606/280; 606/70; 606/286; 606/297; 606/74

(58) Field of Classification Search
CPC ............. A61B 17/746; A61B 17/8061; A61B 17/8085
USPC ............................................. 606/280–299, 74
See application file for complete search history.

(56) References Cited

U.S. PATENT DOCUMENTS

| | | | | |
|---|---|---|---|---|
| 5,718,705 | A * | 2/1998 | Sammarco | 606/284 |
| 6,123,709 | A * | 9/2000 | Jones | 606/281 |
| D469,533 | S * | 1/2003 | Bryant et al. | D24/155 |
| 7,867,260 | B2 * | 1/2011 | Meyer et al. | 606/280 |
| 2004/0087954 | A1 * | 5/2004 | Allen et al. | 606/74 |
| 2004/0210220 | A1 * | 10/2004 | Tornier | 606/69 |
| 2005/0080421 | A1 * | 4/2005 | Weaver et al. | 606/69 |
| 2006/0058795 | A1 * | 3/2006 | Boyd | 606/69 |
| 2006/0217722 | A1 * | 9/2006 | Dutoit et al. | 606/69 |
| 2007/0123886 | A1 * | 5/2007 | Meyer et al. | 606/70 |
| 2008/0119895 | A1 * | 5/2008 | Manceau | 606/280 |
| 2010/0234896 | A1 * | 9/2010 | Lorenz et al. | 606/286 |

FOREIGN PATENT DOCUMENTS

WO WO 2008/019511 * 2/2008 ............. A61B 17/84

* cited by examiner

*Primary Examiner* — Michael T Schaper

(57) ABSTRACT

An orthopaedic fixation component attachable to a femur, said femur defining a femur shaft, a femur head and a femur neck extending therebetween, said femur further defining a greater trochanter limiting laterally said femur neck, said orthopaedic fixation component comprising: a shaft section fixation portion and an end section fixation portion extending substantially longitudinally therefrom, said shaft section and end section fixation portions being respectively securable to said femur shaft and said greater trochanter; said end section fixation portion including a pair of end arms, said end arms being configured, sized and positioned to delimit a trochanter receiving recess for substantially fittingly receiving a prominent portion of said greater trochanter.

22 Claims, 5 Drawing Sheets

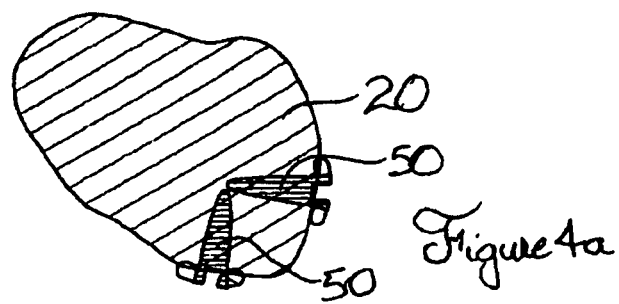
Figure 4a
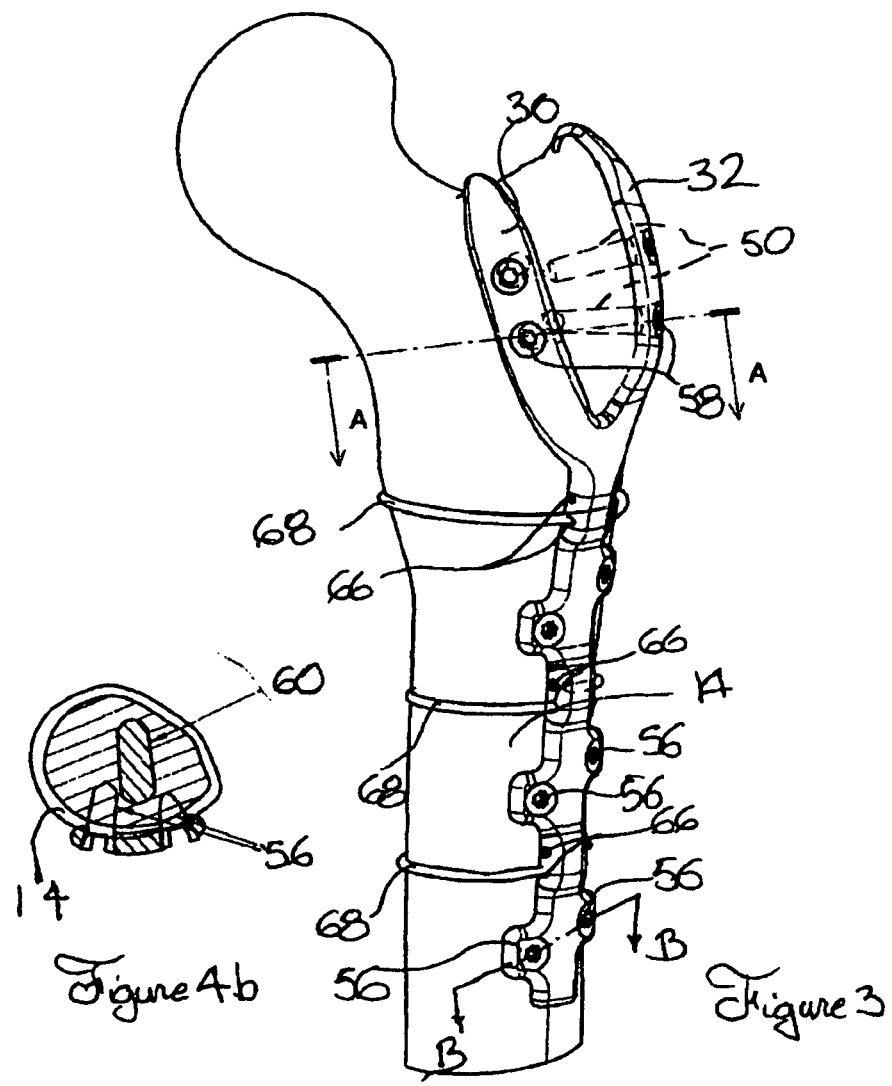
Figure 4b
Figure 3

ORTHOPAEDIC FIXATION COMPONENT AND METHOD

The present application claims priority from U.S. Provisional Patent Application Ser. No. 61/129,221 filed on Jun. 12, 2008.

FIELD OF THE INVENTION

The present invention relates to the general field of orthopaedic surgery components and methods and is particularly concerned with an orthopaedic fixation component and method.

BACKGROUND

There exists a wide variety of situations wherein it is desirable to fixate adjacent bone pieces or segments to promote healing of a fracture. Such situations occur, for example, whenever a fragment of the greater trochanteric portion of the femur bone needs to be fixated to the shaft of the femur.

With the aging demographics of many industrialized countries, hip related surgical procedures are becoming increasingly prevalent. An example of such procedures is the so-called total hip replacement surgery or arthroplasty which is typically performed as a consequence of osteoarthritis of the hip joint. The procedure involves replacing the diseased cartilage and bone of the hip joint with artificial materials including an artificial prosthesis.

During the procedure, a segment of the greater trochanteric portion of the femoral bone is typically temporarily osteotomized, that is a the greater trochanter is surgically separated from the proximal end of the femur so that the soft tissue attached to the greater trochanter can be moved aside in preparation for implantation of the femoral stem of the replacement prosthesis into the medullar canal of the femoral shaft. Once the femoral stem of the prosthesis is seated within the medullar canal in the femur, the greater trochanter is re-attached to the proximal end of the femur.

The greater trochanter is subjected to considerable stress imparted thereon by anatomical structures such as muscles attachments during normal use of the hip. Accordingly, mechanical fixation of the greater trochanter to the femoral shaft is mandatory in order to promote healing of the fracture created by the osteotomizing step of the hip replacement procedure or traumatic injury.

Also, because of the considerable stress imparted on the greater trochanter as a consequence of the total hip arthroplasty procedure, it is estimated that this type of procedure is associated with a relatively high percentage of greater trochanter post-surgical fractures, which, in turn, may require fixation.

Other examples of situations wherein fixation of the greater trochanter to the femur shaft is required include trochanter and/or proximal femur reconstruction, corrective or revision hip surgery and the like.

One relatively common prior art method for fixating the greater trochanter to the proximal femur shaft is a so-called "cerclage" fixation technique wherein a flexible member, such as a cable, is drawn tight and clamped in order to encircle the target fixation site and to hold the bone portions together until they have time to heal.

Typically, the surgical cables are implanted using tensioning devices which apply tension to a surgical cable looped around the bone. Crimps are then added and deformed to clamp the cable loop in place.

The so-called "cerclage" methods, although somewhat useful, are associated with a number of drawbacks. For example, such procedures are typically considered relatively complex. Furthermore, cable failure, migration or loosening may lead to fixation loss and non-union of the bone fragments with clinical consequences such as pain, lack of functionality and the like.

Other types of components have been devised in attempts to provide solutions for fixating the greater trochanter to the femur shaft. For example, some components include a bone grip for engaging over the trochanter and a plate portion for extending down over the shaft of the femur.

A well known typical example of such type of component is the so-called "Cable-Ready" (a registered trade mark) greater trochanteric re-attachment system developed by Zimmer. This system involves the use of a component which has a substantially straight, flat and elongated plate portion, integral with a hooked portion terminating in a spike. Ideally, the hooked grip portion lies over the greater trochanter, and the plate portion overlies the shaft of the femur. Both portions have apertures to receive "cerclage" cables, which are passed around the bone, to secure the device in place.

Again, although somewhat useful, such devices also suffer from numerous drawbacks. Indeed, as is well known, the greater trochanter lies laterally, close to the skin, and can be easily palpated on the lateral side of the thigh. Because it is the most lateral point of the hip region, the greater trochanter may cause discomforts when lateral pressure is exerted on the side of the body such as when an individual lies on his or her side on a hard surface. Most prior art fixation plates increase the discomfort by being located over the most prominent portion of the greater trochanter. Also, some prior art devices require that relatively large incisions be performed in large leg muscles to position them properly over the greater trochanter, with all the discomfort and risk for complications associated with such operations.

Accordingly, there exists a need for an improved orthopaedic fixation component and it is a general object of the present invention to provide such an improved orthopaedic fixation component.

SUMMARY OF THE INVENTION

In a broad aspect, the invention provides an orthopaedic fixation component attachable to a femur, said femur defining a femur shaft, a femur head and a femur neck extending therebetween, said femur further defining a greater trochanter limiting laterally said femur neck, said orthopaedic fixation component comprising: a shaft section fixation portion and an end section fixation portion extending substantially longitudinally therefrom, said shaft section and end section fixation portions being respectively securable to said femur shaft and said greater trochanter; said end section fixation portion including a pair of end arms, said end arms being configured, sized and positioned to delimit a trochanter receiving recess for substantially fittingly receiving a prominent portion of said greater trochanter.

The proposed orthopaedic fixation component is intended to be used in particular with generally elongated bones such as the femur and in particular for greater trochanteric re-attachment although other applications are within the scope of the present invention.

The proposed orthopaedic fixation component provides a variety of advantages for both the surgeon and the intended patient, some of which are disclosed in greater details at the end of the detailed description portion of the present application. In short, the proposed orthopaedic fixation component is designed so as to improve fixation while reducing post-operative complications.

The present invention also relates to a method of using an orthopaedic fixation component in order to also improve fixation while reducing post-operative complications.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

An embodiment of the present invention will now be disclosed, by way of example, in reference to the following drawings, in which:

FIG. 3, in a perspective view similar to that of FIG. 1, illustrates the insertion within the bone of some of the attachment screws used with the orthopaedic fixation component in accordance with the present invention;

FIG. 4a, in a transversal cross-sectional view taking along arrows A-A of FIG. 3, illustrates the spatial relationship between the inserted attachment screws shown in FIG. 3;

FIG. 4b, in a transversal cross-sectional view taking along arrows B-B of FIG. 3, illustrates the spatial relationship between shaft attachment screws shown in FIG. 3 and the stem of a replacement prosthesis;

DETAILED DESCRIPTION

Figure 1:
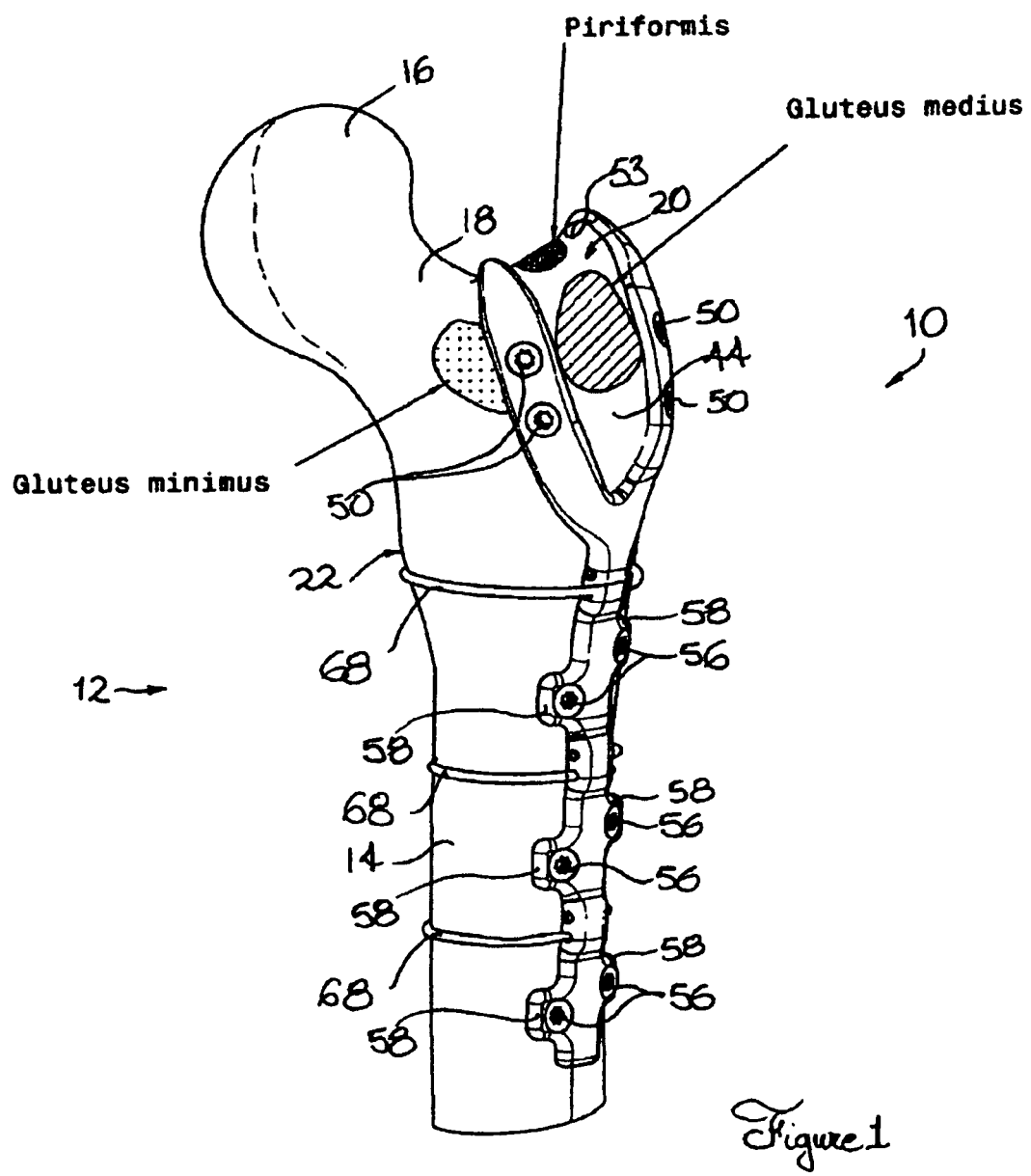
FIG. 1, in a perspective view, illustrates an orthopaedic fixation component in accordance with an embodiment of the present invention operatively mounted on a femoral bone, only a proximal portion of which is shown.

Referring to FIG. 1, there is shown, in a perspective view, a fixation component in accordance with an embodiment of the present invention, generally indicated by the reference numeral 10. The fixation component 10 is shown, by way of example, mounted to a femur generally indicated by reference numeral 12. It should, however, be understood that the fixation component 10 is only shown mounted to a femur 12 by way of example and that the fixation component 10 could be used for fixating or securing bone segments located at other anatomical regions without departing from the present invention.

More specifically, the fixation component 10 is particularly well adapted to be used at anatomical regions involving substantially elongated bones defining a corresponding bone end region. By way of non limitative examples, the fixation component 10 could, for example, be used in applications involving the distal femur, the proximal tibia as well as the proximal and distal humerus regions.

Figure 2:
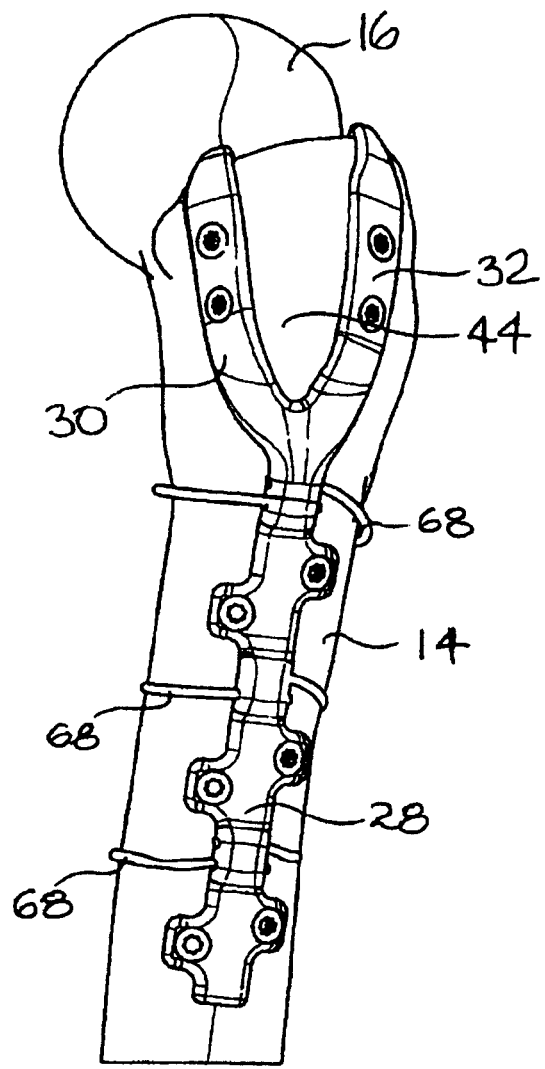
FIG. 2, in a front view, illustrates the orthopaedic fixation component and femoral bone shown in FIG. 1.

As is well known, the femur 12 is an elongated bone. As shown in FIGS. 1 through 3, the femur 12 includes a body or shaft 14 defining a pair of longitudinally opposed extremities or ends (only the proximal one of which is shown in the Figures). The body or shaft 14 of the femur is slightly bowed inferiorly and is narrowest at its mid-point. Its middle two quarters are approximately circular in transverse section. The distal end (not shown) of the femur shaft 14 is broadened by medial and lateral condyles where it articulates with the tibia and patella to form the knee joint.

The proximal end, shown in FIG. 1, includes a femur head 16, a femur neck 18, a greater trochanter 20 and a lesser trochanter 22. As is also well known, the femur head 16 is typically smooth and forms ⅔ of a sphere. It is directed medially, superiorly, and slightly inferiorly to fit into the acetabulum of the hip bone (not shown).

The femur neck 18 connects the femur head 16 to the femur body or shaft 14, typically at an angle of approximately 125 degrees. The femur neck 18 is limited laterally by the greater trochanter 20 and is narrowest in diameter at its mid-section. A broad, rough inter-trochanteric line runs infero-medially from the greater trochanter. This inter-trochanteric line passes inferior to the lesser trochanter and becomes continuous with the spiral line on the posterior aspect of the femur.

The inter-trochanteric line is produced by the attachment of the massive illio-femoral ligament (not shown). The inter-trochanteric line separates the interior surface of the femur neck 18 from the femur body or shaft 14 of the femur 12. A prominent ridge, the inter-trochanteric crest, unites the two trochanters 20, 22 posteriorly.

In the anatomical position, a line joining the tips of the greater trochanters 20 normally passes through the center of the femur heads 16 (only on of which is shown) and the pubic tubercies (not shown). As shown more specifically in FIG. 2, the greater trochanter 20 of the femur 12 is a substantially large, somewhat rectangular projection from the junction of the femur neck 18 and the femur body 14. It provides an attachment for several muscles of the gluteal region. Some of these muscular attachments are illustrated schematically in FIG. 1.

As is well known, both the gluteus medius and the gluteus minimus are used for abduction and medial rotation of the thigh as well as to steady the pelvis. The distal attachment of the gluteus medius is typically located on the lateral surface of the greater trochanter 20 while the distal attachment of the gluteus minimus is typically located on the anterior surface of the greater trochanter 20.

The obturator internus and the gemelli, superior and inferior, are used for laterally rotating the extended thigh and abducting the flexed thigh. They are also used to steady the femur head 16 in the acetabulum (not shown). Both the obturator internus and the gemini superior and inferior have their distal attachment on the medial surface of the greater trochanter 20.

Another muscle having its distal attachment on the greater trochanter 20 is the piriformis muscle attached to the superior border of the greater trochanter 20. It should be understood that the muscular insertions illustrated in FIG. 1 are rough schematic representations of the three major muscle groups hereinafter discussed and should only be considered an approximation of the actual anatomical reality.

Figure 6:
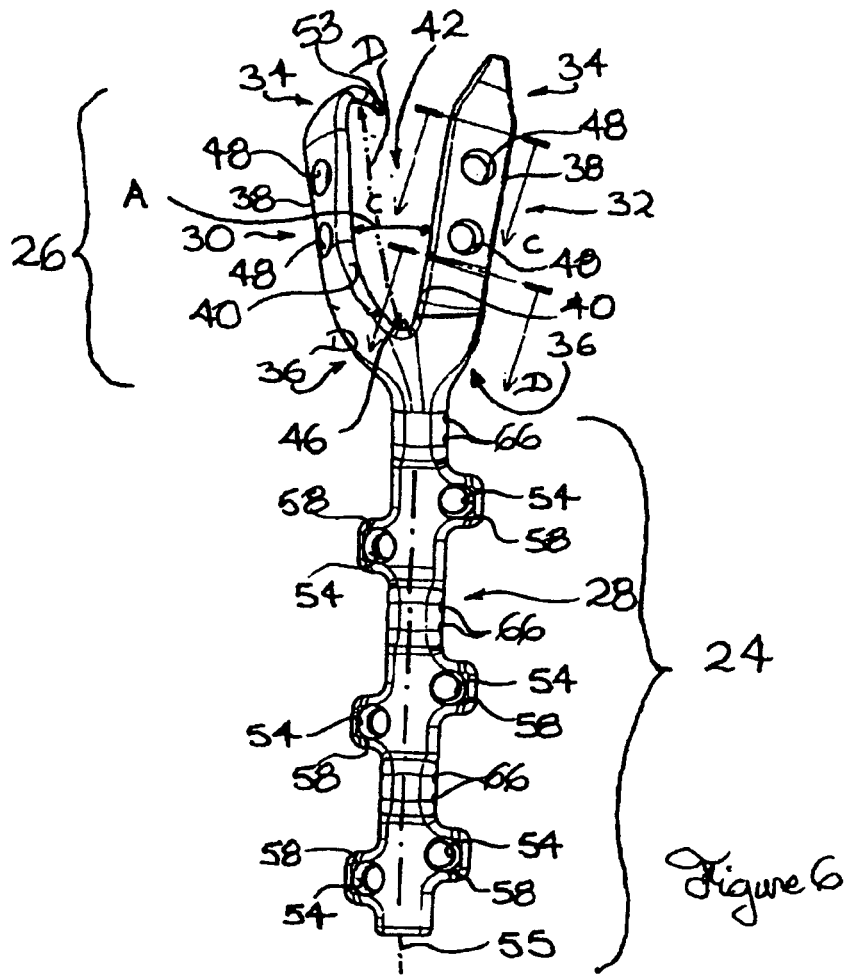
FIG. 6, in a front view, illustrates the orthopaedic fixation component shown in FIGS. 1 through 5.

Referring now more specifically to FIG. 6, there is shown in greater details some of the features of the fixation component 10. In general terms, the fixation component 10 includes a shaft section fixation portion 24 and a substantially longitudinally and integrally extending end section fixation portion 26 for being respectively secured to a corresponding shaft section and a corresponding end section of bone such as the femur shaft 14 and the greater trochanter 20 shown in FIG. 1 through 3.

In the preferred embodiment, the fixation component 10 has a generally asymmetrical "Y"-shaped configuration defining a shaft arm generally indicated by the reference numeral 28 attached to a pair of end arms generally indicated by the reference numerals 30 and 32.

The end arms 30, 32 typically extend integrally from the shaft arm 28 although they may be permanently or reversibly attached to the latter without departing from the scope of the present invention. Also, in the embodiment shown throughout the Figures, the shaft arm 28 and the end arms 30, 32 are rigidly secured to each other in a substantially stable spatial relationship relative to each other.

However, in other embodiments of the invention (not shown) the shaft arm 28 and the end arms 30, 32 could be pivotally, slidably or otherwise movably connected to each other so as to allow for selective spatial movement therebetween in predetermined combinations. For example, both end arms 30, 32 could be fixedly secured to each other while being movably secured to the shaft arm 28. Alternatively, the end arms 30, 32 could be movable relative to each other.

In instances wherein the shaft arm 28 and/or the end arms 30, 32 are movable relative to each other, the fixation component 10 may further be provided with arm movement preventing means for either permanently or releasably selectively preventing the relative movements between the shaft arm 28 and one or both of the end arms 30, 32.

The end arms 30, 32 are typically configured, sized and positioned so as to diverge away from each other, together forming a substantially asymmetrical V-shaped configuration. Each one of the end arms 30, 32 has a substantially elongated configuration defining a corresponding end arm proximal section 34 and a longitudinally opposed end arm distal section 36. Typically, the end arm distal sections 36 of each end arm 30, 32 merge integrally with each other.

Each one of the end arms 30, 32 also defines a corresponding end arm outer edge 38 and a substantially transversely opposed end arm inner edge 40. The end arm inner edges 40 together define a trochanter receiving recess 42 extending therebetween for receiving at least a selected portion of the greater trochanter 20. The selected portion of the greater trochanter 20 adapted to be received within the trochanter receiving recess 42 is typically a particularly prominent or protruding portion 44 (seen in FIG. 1) of the greater trochanter 20.

One of the main features of the present invention resides in that the end arms 30, 32 are configured, sized and positioned such that the trochanter receiving recess 42 substantially fittingly receives the prominent portion 44 of the greater trochanter 20. More specifically, the end arms 30, 32 are configured, sized and positioned such that the opposed end arms inner edges 40 substantially partially encircle the prominent portion 44 of the greater trochanter 20.

The end arm inner edges 40 typically merge with each other about their respective end arm distal sections 36 so as to form a nadir 46. The end arms 30, 32 are typically further configured, sized and positioned such that the nadir 46 is located substantially underneath the prominent portion 44 of the trochanter 20 when the fixation component 10 is operatively mounted on the femur 12.

Another feature of the present invention resides in that the end arms 30, 32 are configured, sized and positioned relative to each other so as to optimize the retaining action exerted thereby on the greater trochanter 20 so as to prevent relative movement between trochanteric portions and lessen the probability of creating a secondary fracture.

The end arms 30, 32 provide a multi-directional holding action adapted to cancel out the tendency of the three major muscles of which the distal insertion is shown in FIG. 1 tending to exert a pulling action upon the greater trochanter 20 along multiple vectorial directions. This holding action prevents the trochanteric portions from being pulled in any one of the vectorial directions and, in particular, any one of the three major directions illustrated in FIG. 1. The specific configuration, size and position of the end arms 30, 32 is also adapted to take into account that there is an intense and strong pull, particularly of the abductor muscles of the hip during normal activities of daily living such as ambulation.

The end arms 30, 32 are each provided with an end arm attachment means for attaching or anchoring the end arms 30, 32 to the greater trochanter 20. In the preferred embodiment, the end arm attachment means includes at least one and preferably two end arm fastening apertures 48 extending through corresponding end arms 30 or 32.

Each end arm fastening aperture 48 is adapted to receive a corresponding fastening component such as an end arm bone screw 50 (seen for example in FIG. 1). Typically, each end arm fastening aperture 48 has a substantially countersunk portion. Typically, although by no means exclusively, the end arm bone screws 50 are of the self-locking type. Self-locking type screws are typically preferred, at least in part, because of the relatively thin layer of the cortex of the bone in the regions of the greater trochanter 20.

Figure 5:
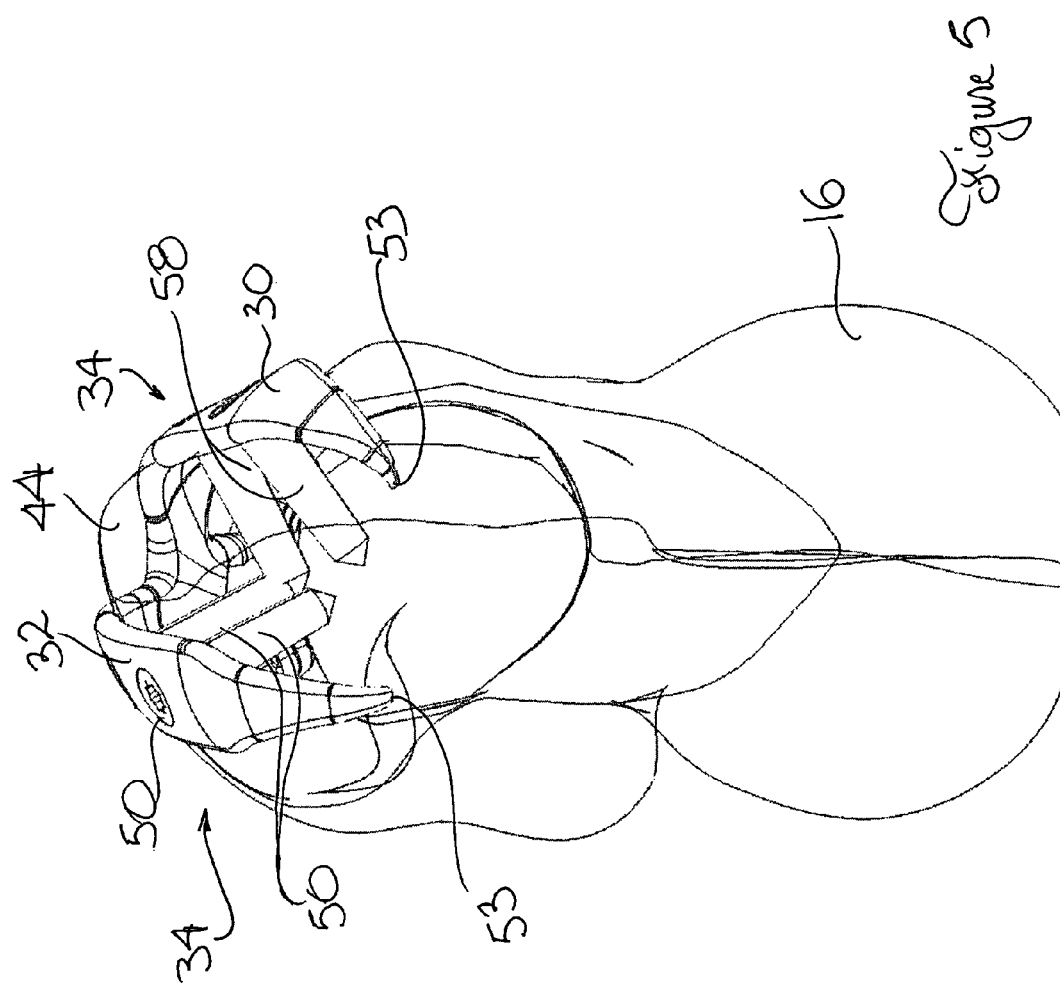
FIG. 5, in a top view, illustrates some of the features of the proximal portion of the orthopaedic fixation component in FIGS. 1 through 4 when the latter is anchored to the femoral bone shown in FIGS. 1 through 3.

As illustrated more specifically in FIG. 3 through 5, the configuration, size and position of the end arms 30, 32 and their corresponding end arm fastening apertures 48 is such that the end arm bone screws 50 provide an entrapment effect for further preventing trochanteric portions from being fractured or pulled out by various forces acting thereon.

The configuration, size and position of the end arms 30, 32 is also chosen in order to take into consideration the position of the insertion of the main muscle attachments on the greater trochanter 20.

Referring back to the schematically illustrated muscular insertions of FIG. 1, it can be seen, the end arms 30, 32 are configured, sized and positioned so that their respective inner and outer peripheral edges 40, 38 substantially clear these muscular attachments or, at least, minimally interfere therewith so as to reduce the risks of clinical problems once the fixation component 10 is operationally attached to the femur 12 and also so as to facilitate the anchoring of the fixation component 10 to the femur 12 during surgery.

As shown more specifically in FIG. 6, the end arms 30, 32, typically diverge away from each other in a proximal direction so as to define an end arm angle "A" therebetween, Typically, although by no means exclusively, the end arm angle "A" has a value of between 60 and 120 degrees.

Figure 7:
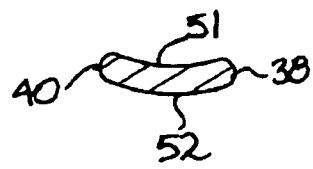
FIG. 7, in a transversal cross-sectional view, illustrates the cross-sectional configuration of an end arm, part of the orthopaedic fixation component, the cross-section being taken across line C-C of FIG. 6.
Figure 8:
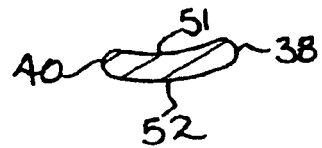
FIG. 8, in a transversal cross-sectional view, illustrates the cross-sectional configuration of an end arm, the cross-section being taken along lines D-D of FIG. 6.

Another feature of the present invention resides in the cross-sectional configuration of at least one and preferably both end arms 30, 32. As illustrated more specifically in FIGS. 7 and 8, each end arm 30, 32 preferably has a substantially concave end arm inner surface 51 and a substantially convex end arm outer surface 52. Also, each of the end arms 30, 32 is also provided with substantially rounded end arm inner and outer edges 40, 38.

The substantially concave end arm inner surface 51 is typically variable along the length of the end arms 30, 32 and adapted to allow for an improved contact engagement between the end arm inner surfaces 51 and the substantially convex outer surface of the greater trochanter 20.

The substantially arc-shaped cross-sectional profile of the end arms 30, 32 is also adapted to increase the structural strength thereof and, hence, allow for minimization of the overall thickness of the end arms 30, 32 for a given material and considering given auxiliary geometrical variables. The optimized fit between the contact surfaces of the end arm inner surface 51 and the outer surface of the greater trochanter 20 combined with the relatively small cross-sectional distance between the end arm inner and outer surfaces 51, 52 is adapted to provide greater comfort to the patient with reduced risks of clinical complications.

As illustrated more specifically in FIGS. 1 through 5, the end arm proximal portion 34 of at least one and typically both end arms 30, 32 typically curves inwardly so as to substantially override at least a portion of the greater trochanter 20 and in operational position provide a retaining means against axial displacement of portions thereof.

Also, at least one and preferably both of the end arms 30, 32 typically taper proximally so as to define a corresponding substantially pointed anchoring apex 53. Typically, the pointed apex 53 is adapted to be inserted into the cortical portion of the upper portion of the greater trochanter 20. Typically, although by no means exclusively, the distance D between the apex 53 and the nadir 46 has a value of between 40 and 70 millimeters.

Alternatively, in an embodiment of the invention not shown, the end arm proximal portion 34 of at least one of the end arms 30, 32 could be deprived of a pointed apex 53 and/or made out of a substantially deformable material so as to allow the surgeon to bend the latter to a suitable shape for increasing the retention characteristics thereof.

Referring back to FIGS. 1 through 3 and 6, there is shown that the shaft arm 28 typically has a substantially elongated configuration defining a shaft arm longitudinal axis 55 (shown in FIG. 6). Another feature of the present invention resides in that the substantially V-shaped configuration formed by the end arms 30, 32 is preferably substantially or laterally offset relative to the shaft arm longitudinal axis 55.

Since the main muscular attachments to the greater trochanter 20 are located substantially anteriorly, the end arms 30, 32 are typically offset substantially posteriorly relative to the shaft arm longitudinal axis 55 so as to reduce the risk of interference or obstruction with the muscles attached to the greater trochanter 20. Typically, as illustrated throughout the Figures, the end arm 32 being operatively mounted more anteriorly than the end arm 30, the end arm 32 is positioned so as to extend at lesser angle relative to the shaft longitudinal axis 55 than the end arm 30.

The shaft arm 28 is provided with a suitable shaft arm attachment means for attaching the shaft arm 28 to the femur shaft 14. In the embodiment shown throughout the Figures, the shaft arm attachment means includes shaft arm attachment apertures 54 for receiving suitable attachment components such as shaft arm screws 56 (seen for example in FIG. 1). The shaft arm attachment apertures 54 are typically provided with a countersunk section.

Each shaft arms attachment aperture 54 typically extends through a corresponding shaft arm flange or tab 58 extending integrally and substantially laterally from the shaft arm 28. The shaft arm flanges or tabs 58 and their corresponding shaft arm attachment apertures 54 are positioned in an offset relationship relative to each other so as to prevent the shaft arm screws 56 from interfering with each other when the fixation component 10 is operatively mounted.

Typically, the shaft arm tabs 58 and corresponding shaft arm attachment apertures 54 are grouped in pairs with members of a given pair extending in laterally opposite and longitudinally offset relationships relative to each other.

As illustrated more specifically in FIG. 4b, the shaft arm attachment apertures 54 are positioned so as to no only provide sufficient clearance between the shaft arm screws 56 but also to so as to reduce the risks of interference with the femoral stem 60 of a hip replacement prosthesis when the fixation component 10 is used on a femur 12 having such a prosthesis.

The shaft arm attachment means typically further includes "cerclage" cable channels 66 extending substantially transversely across the shaft arm 28 for receiving "cerclage" cables 68. Typically, although by no means exclusively, a pair of cerclage cable channels 66 extends through the shaft arm 28 proximally to each pair of shaft arm attachment apertures 54.

The fixation component 10 could be provided with "cerclage" cables 68 already having a portion thereof secured to the shaft arm 28 or be simply adapted to receive conventional "cerclage" cables such as the Zimmer Co—Cr cables.

Alternatively, the fixation component 10 could be provided with or used in conjunction with a "cerclage" cable 68 made out of a super-elastic material. Preferably, although by no means exclusively, the super-elastic "cerclage" cable could be of the type having a braided tuberous structure. Such a cable is described in the PCT application bearing Serial No. PCT/CA2005/001859, naming Brailovski et al as inventors, the entire content of which is expressly incorporated herein by reference thereto.

Super-elastic cables having a braided tuberous structure provide a synergistic advantage when used with the hereinabove disclosed fixation component 10 by reducing the contact pressure on connected bones and maintaining compression between fragments during the fracture healing period.

In use, the specific configuration and size of the various sections of the fixation component 10 allows a surgeon to position the fixation component 10 on the femur 12 of an intended patient in such a manner that the end arms 30, 32 are strategically positioned to reduce the risk of having portions or fragments of the greater trochanter 20 being displaced or pulled out of alignment relative to their optimal anatomical relationship with the femur shaft 14.

The configuration, size and relative position of the end arms 30, 32 relative to the shaft arm 28 take into consideration both the orientation and magnitude of the forces exerted by the muscles attached to the greater trochanter 20 and the insertion location of such muscles in, order to reduce the risk of interference therewith.

The retaining action exerted by the end arms 30, 32 on portions or fragments of the greater trochanter 20 is compounded by the strategic location of end arm fastening apertures 48 adapted to receive self-locking bone screws oriented to provide an entrapment effect.

Furthermore, the configuration of the fixation component 10 is designed in such a manner that the outward radial protrusion of the end arms 30, 32 away from the greater trochanter 20 is also minimized. Indeed, as mentioned previously, the end arms 30, 32 are configured, sized and positioned relative to the shaft arm 28 in such a manner that they create a trochanter receiving recess therebetween, the trochanter receiving recess 42 being, in turn, configured and sized for substantially fittingly circumventing the prominent portion 44 of the greater trochanter 20.

Also, as mentioned previously, the configuration of the end arms 30, 32, including their cross-sectional configuration, is such that the fit with the surface of the greater trochanter 20 is optimized and the structural characteristics of the end arms 30, 32 is improved, allowing for a thinner structure. The avoidance of the prominent portion 44 of the greater trochanter 20 synergistically combined with the improved contact with the greater trochanter 20 and the relatively thin profile reduces the protrusion of the end arms 30, 32 from the femur 12 translates not only into an improved aesthetical appearance but also a greater comfort for the patient.

The shaft arm attachment means provided with the fixation component 10 allows the latter to be used with a wide variety of patients including patients requiring total hip arthroplasty prosthesis. Indeed, the strategic positioning of the shaft arm attachment apertures 54 allows for a suitable number of shaft arm screws 56 to be used in order to solidly anchor the shaft arm 28 to the femur shaft 14 while reducing the risk of interference of the shaft arm screws 56 not only with adjacent shaft arm screws 56 but also with the femoral stem 60 of a hip replacement prosthesis inserted within the medullary canal of the femur 12 such as shown in FIG. 4b.

Furthermore, the "cerclage" cable channels 66 allow for the use of either conventional "cerclage" cables 68 or so-called super-elastic cables 68. The use of super-elastic cables 68 and, in particular, super-elastic cables 68 having a braided tubular structure provides a synergistic effect when combined with the other features of the fixation component 10.

By reducing the contact pressure on contacted bones, these cables 68 allow for the fixation component 10 to be used with patients having particularly fragile bone structures. Also, such cables 68 are adapted to maintain a compression force between fragments during the fracture healing period which is particularly crucial with such patients.

Furthermore, the positioning of the "cerclage" cable channels 66 in an alternating fashion with pairs of shaft arm attachment apertures 54 provides an optimal distribution of force exerted on the bone structure for obtaining secure anchorage while reducing the risk of traumatizing the femur shaft 14.

The present invention also relates to a method of using an orthopaedic fixation component such as the hereinabove disclosed fixation component 10 or other suitable fixation components. The orthopaedic method, in accordance with the present invention, includes positioning a fixation component to a bone structure defining a bone shaft and a bone end section having a prominent region in such a manner that the fixation component substantially avoids the prominent section while providing an efficient retaining action for preventing relative displacement between the bone structures.

The proposed orthopaedic method also includes as an independent or combined step the use of a "cerclage" cable made out of a super-elastic material for attaching the fixation component to the bone. Preferably, the step of using a "cerclage" cable includes using a super-elastic "cerclage" cable having a braided structure for attaching the fixation component to the bone structure.

Although the present invention has been described hereinabove by way of preferred embodiments thereof, it can be modified, without departing from the spirit and nature of the subject invention as defined in the appended claims.

What is claimed is:

1. A fixation component securable to a femur, said femur defining a femur shaft and a greater trochanter extending from said femur shaft, said greater trochanter defining an anterior facet and a lateral facet, said fixation component comprising:
   a shaft section fixation portion, said shaft section fixation portion including a substantially elongated shaft arm defining a shaft arm longitudinal axis; and
   an end section fixation portion extending substantially longitudinally from said shaft section fixation portion, said end section fixation portion defining a pair of end arms extending substantially away from said shaft fixation portion, each one of said end arms defining a corresponding end arm outer edge and a substantially transversely opposed end arm inner edge, said end arm inner edges of said end arms together defining a trochanter receiving recess extending therebetween, said trochanter receiving recess being configured and sized for receiving at least a selected portion of said greater trochanter, said selected portion of said greater trochanter being a prominent portion of said greater trochanter that protrudes from adjacent portions of said greater trochanter, said end arms being configured, sized and positioned such that said trochanter receiving recess substantially fittingly receives said prominent portion of said greater trochanter;
   said shaft section fixation portion and said end section fixation portion being configured and sized so as to be respectively securable to said femur shaft and to said greater trochanter;
   wherein said end arms are configured, sized and positioned so as to converge toward each other in a direction leading substantially toward said shaft arm, said end arms together forming a substantially V-shaped configuration, said V-shaped configuration being laterally asymmetrical relative to said shaft arm longitudinal axis, each of said end arms defining a corresponding end arm proximal section and a substantially longitudinally opposed end arm distal section, said end arm distal sections of said end arms merging integrally with each other at a merging location;
   said end arms being also configured, sized and positioned such that one of said end arms is securable to said anterior facet and another one of said end arms is securable to said lateral facet when said fixation component is operatively secured to said greater trochanter.

2. A fixation component as defined in claim 1, wherein said fixation component has a generally asymmetrical substantially "Y"-shaped configuration.

3. A fixation component as defined in claim 2, wherein said end arms both extend integrally from said shaft arm.

4. A fixation component as defined in claim 3, wherein said shaft arm and said end arms are rigidly secured to each other in a substantially stable spatial relationship relative to each other.

5. A fixation component as defined in claim 1, wherein said end arm proximal sections each define a respective free end and said end arms are disjoint from each other between said merging location and said free ends.

6. A fixation component as defined in claim 5, wherein each of said end arms define a substantially concave end arm inner surface and a substantially convex end arm outer surface located substantially opposed to said end arm inner surface, each of said end arms also defining at least one end arm fastening aperture extending therethrough between said end arm inner and outer surfaces, said at least one end arm fastening apertures of said two arms being angled relative to each other.

7. A fixation component as defined in claim 1 wherein said end arms define an end arm midway axis extending midway between said end arms, said end arm midway axis being angled relative to said shaft arm longitudinal axis.

8. A fixation component as defined in claim 1, wherein said end arms are configured, sized and positioned such that said end arms inner edges substantially partially encircle said prominent portion of said greater trochanter.

9. A fixation component as defined in claim 8, wherein said end arm inner edges merge with each other substantially adjacent to said shaft arm so as to form a nadir, said end arms being further configured, sized and positioned such that said nadir is located substantially underneath said prominent portion of said greater trochanter when said fixation component is operatively mounted on said femur.

10. A fixation component as defined in claim 1, wherein said end arms are each provided with a respective end arm attachment for attaching said end arms to said greater trochanter.

11. A fixation component as defined in claim 10, wherein said end arm attachments each include at least one end arm fastening aperture extending through a respective one of said end arms.

12. A fixation component as defined in claim 1, wherein at least one of said end arms defines a substantially concave end arm inner surface and a substantially convex end arm outer surface located substantially opposed to said end arm inner surface.

13. A fixation component as defined in claim 1, wherein at least one of said end arms tapers in a direction leading substantially away from said shaft arm so as to define a substantially pointed anchoring apex.

14. A fixation component as defined in claim 1, wherein said shaft arm is provided with a shaft arm attachment for attaching said shaft arm to said femur shaft.

15. A fixation component as defined in claim 14, wherein said shaft arm attachment includes shaft arm attachment apertures for receiving suitable attachment components.

16. A fixation component as defined in claim 15, wherein said shaft arm defines a shaft arm flange extending substantially laterally from the remainder of said shaft arm, at least one of said arm attachment apertures extending through said shaft arm flange.

17. A fixation component as defined in claim 16, wherein said shaft arm defines a plurality of shaft arm flanges each extending integrally and substantially laterally from the remainder of said shaft arm, at least one respective one of said arm attachment apertures extending through each of said shaft arm flanges.

18. A fixation component as defined in claim 17, wherein said shaft arm flanges are grouped in pairs with members of a given pair extending in substantially laterally opposite and substantially longitudinally offset relationships relative to each other.

19. A fixation component as defined in claim 17, wherein said shaft arm attachment further includes cerclage cable channels extending substantially transversely across said shaft arm for receiving cerclage cables.

20. A fixation component as defined in claim 19, wherein a pair of cerclage cable channels extends through said shaft arm proximally to each pair of shaft arm flanges.

21. A fixation component as defined in claim 17, wherein at least a subset of said shaft arm flanges extend generally in a lateral plane, a projection of said V-shaped configuration in said lateral plane being laterally asymmetrical relative to a projection of said shaft arm longitudinal axis in said lateral plane.

22. A fixation component as defined in claim 1, wherein said fixation component is provided with cerclage cables having a portion thereof secured to said shaft arm.

* * * * *